United States Patent [19]

Chou et al.

[11] Patent Number: 4,992,616
[45] Date of Patent: Feb. 12, 1991

[54] HETEROGENEOUS ISOPARAFFIN/OLEFIN AKLYLATION PROCESS

[75] Inventors: Tai-Sheng Chou, Pennington, N.J.; Albin Huss, Jr., Chadds Ford; Clinton R. Kennedy, West Chester, both of Pa.

[73] Assignee: Mobil Oil Corporation, New York, N.Y.

[21] Appl. No.: 425,497

[22] Filed: Oct. 17, 1989

Related U.S. Application Data

[63] Continuation of Ser. No. 219,130, Jul. 15, 1988, abandoned.

[51] Int. Cl.$^5$ .............................................. C07C 2/58
[52] U.S. Cl. ................................... 585/722; 585/726; 585/728
[58] Field of Search ..................... 585/722, 726, 728

[56] References Cited

U.S. PATENT DOCUMENTS

| | | | |
|---|---|---|---|
| 2,363,116 | 11/1944 | Bruner | 585/725 |
| 2,450,764 | 10/1948 | Meyers | 585/744 |
| 2,843,642 | 7/1958 | Kelly | 585/726 |
| 2,939,890 | 6/1960 | Hervert et al. | 585/463 |
| 3,131,230 | 4/1964 | Hervert et al. | 585/463 |
| 3,251,902 | 5/1966 | Garwood et al. | 585/722 |
| 3,450,644 | 6/1969 | Lanewala et al. | 502/38 |
| 3,541,180 | 11/1970 | Thomas | 585/722 |
| 3,549,557 | 12/1970 | Bolton et al. | 502/73 |
| 3,624,173 | 11/1971 | Kirsch et al. | 585/467 |
| 3,644,565 | 2/1972 | Biale | 585/722 |
| 3,647,916 | 3/1972 | Caesar et al. | 585/722 |
| 3,655,813 | 4/1972 | Kirsch et al. | 585/722 |
| 3,706,814 | 12/1972 | Kirsch et al. | 585/722 |
| 3,738,977 | 6/1973 | Biale | 526/108 |
| 3,840,613 | 10/1974 | Eberly, Jr. et al. | 585/722 |
| 3,862,258 | 1/1975 | Huang et al. | 585/726 |
| 3,917,738 | 11/1975 | Fenske et al. | 585/722 |
| 4,384,161 | 5/1983 | Huang | 585/722 |

*Primary Examiner*—Curtis R. Davis
*Attorney, Agent, or Firm*—Alexander J. McKillop; Charles J. Speciale; Malcolm D. Keen

[57] ABSTRACT

The quality of alkylate resulting from the alkylation of isoparaffin with olefin in the presence of an alkylation catalyst comprising a large pore zeolite, e.g., zeolite Beta, and a Lewis acid, e.g., $BF_3$, is significantly improved by the presence of added water in the alkylation reaction zone.

23 Claims, 1 Drawing Sheet

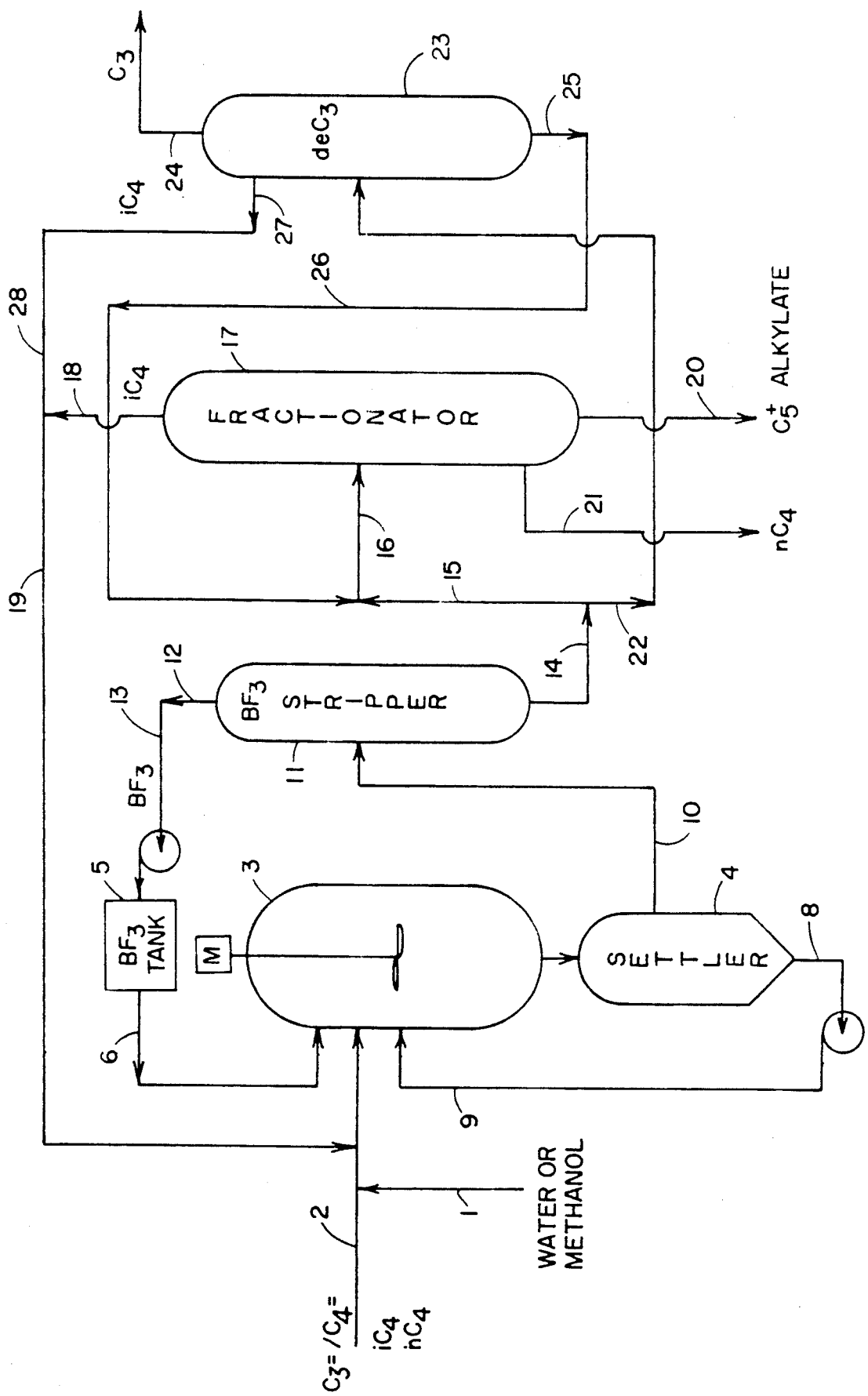

HETEROGENEOUS ISOPARAFFIN/OLEFIN AKLYLATION PROCESS

This is a continuation of copending application Ser. No. 219,130, filed on July 15, 1988, now abandoned.

BACKGROUND OF THE INVENTION

The present invention relates to alkylating an isoparaffin with olefin to provide an alkylate product useful as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-olefin alkylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$-$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88–94 percent by the continuous addition of fresh acid and the continuous withdrawal of spent acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable and more selective alkylation process than the currently used hydrofluoric and sulfuric acid alkylation processes.

The alkylation process of U.S. Pat. No. 3,862,258 utilizes a catalyst comprising a macroreticular acid cation exchange resin and boron trifluoride. It is reported in this patent that the life of such a catalyst can be extended by the presence in the reaction mixture of closely controlled amounts of water which can be added to the feed as water or as a water-forming compound, for example, in the form of an alcohol such as methanol.

Crystalline metallosilicates, or zeolites, have also been widely investigated for use in the catalysts of alkylation. For example, U.S. Pat. No. 3,251,902 describes the use of a fixed bed of ion-exchanged crystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin molar ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_{5+}$ paraffins such as Udex raffinate or $C_{5+}$ olefins to the alkylation reactor feed and the use of specific reactant proportions, halide adjuvants, etc.

U.S. Pat. No. 3,624,173 discloses the use, in isoparaffin-olefin alkylation, of crystalline aluminosilicate zeolites containing gadolinium.

U.S. Pat. No. 3,738,977 discloses alkylation of paraffins with ethylene employing a zeolite catalyst which possesses a Group VII metal component, the catalyst having been pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

SUMMARY OF THE INVENTION

It has now been discovered that in an alkylation process in which an isoparaffin is reacted with an olefin in the presence of a large pore zeolite and a Lewis acid to provide an alkylate product, an improvement in the quality of the alkylate is obtained by carrying out the alkylation in the presence of added water and/or water-producing material.

BRIEF DESCRIPTION OF THE DRAWING

The invention is described in connection with the accompanying drawing, a schematic representation of an embodiment of the alkylation process herein.

DESCRIPTION OF THE PREFERRED EMBODIMENTS

Zeolites used in the present invention include those which have pores sufficiently large to physically absorb 2,2,4-trimethylpentane such as, for example, ZSM-3, ZSM-4, ZSM-12, ZSM-18, ZSM-20, zeolite Beta, zeolite L, mordenite, faujasite, zeolite Y, and the rare earth metal-containing forms of the above. A wide range of silica-to-alumina ratios, e.g., from at least about 10:1 to about 200:1 and even higher, e.g., approaching infinity, can be used. For the purposes of this invention, zeolite Y includes zeolite Y in its as synthesized form, as well as its variant forms including framework dealuminated zeolite Y, e.g., ultrastable Y (USY) described in U.S. Pat. No. 3,293,192 and LZ-210 described in U.S. Pat. No. 4,503,023.

The large pore zeolite selected for use in the improved alkylation process of this invention generally can possess an alpha value over a wide range of from less than 1 to over 1000. "Alpha value", or "alpha number", is a measure of zeolite acidic functionality and is more fully described together with details of its measurement in U.S. Pat. No. 4,016,218, J. Catalysis, 6, pp. 278-287 (1966) and J. Catalysis, 61, pp. 390-396 (1980). Zeolites of low acidity (alpha values of less than about 200) can be achieved by a variety of techniques including (a) synthesizing a zeolite with a high silica/alumina ratio, (b) steaming, (c) steaming followed by dealuminization and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° with from about 10 to about 200 atmospheres. Specific details of several steaming procedures may be gained from the disclosures of U.S. Pat. Nos. 4,325,994, 4,374,296 and 4,418,235, the contents of which are incorporated by reference herein. Aside from, or in addition to any of the foregoing procedures, the surface acidity of the zeolite can be eliminated or reduced by treatment with bulky reagents as described in U.S. Pat. No. 4,520,221, the contents of which are incorporated by reference herein.

In practicing the improved alkylation process of the present invention, it may be advantageous to incorporate the above-described large pore zeolites into some other material, i.e., a matrix or binder, which is stable under the conditions employed in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolites employed herein can be composited with a porous matrix material such as carbon, alumina, titania, zirconia, silica, silica-alumina, silica-magnesia, silica-zirconia, silica-thoria, silica-beryllia, silica-titania, etc., as well as ternary oxide compositions, such as silica-alumina-thoria, silica-aluminazirconia, silica-alumina-magnesia, silica-magnesia-zirconia, etc. The matrix can be in the form of a cogel. The relative proportions of zeolite component and matrix material, on an anhydrous basis, can vary widely with the zeolite content ranging from between 1 to about 99 wt %, and more usually in the range of about 5 to about 90 wt % of the dry composite.

In some cases, it may be advantageous to provide the zeolite component of the alkylation catalyst herein as an extrudate bound with a low acidity refractory oxide binder employing the method described in commonly assigned, copending U.S. patent application Ser. No. 44,639, filed May 1, 1987, and now abandoned, the contents of which are incorporated by reference herein. In accordance with said method, a homogeneous mixture of a large pore zeolite such as zeolite Beta, water and a low acidity refractory oxide binder, e.g., silica, which contains at least an extrusion-facilitating amount of the binder provided in a colloidal state and which is substantially free of added alkali metal base and/or basic salt, is formed into an extrudable mass, the mass is extruded and the resulting extrudate is dried and calcined.

The original cations associated with the zeolite utilized herein can be replaced by a wide variety of other cations according to techniques well known in the art, e.g., by ion-exchange. Typical replacing cations include hydrogen, ammonium, alkyl ammonium and metal cations, and their mixtures. In the case of metal cations, particular preference is given to such metals as magnesium, zinc, calcium, zinc, and mixtures thereof. A typical ion-exchange technique involves contacting the particular zeolite with a salt of the desired replacing cation. Although a wide variety of salts can be employed, particular preference is given to chlorides, nitrates and sulfates. Representative ion-exchange techniques are disclosed in a number of patents including U.S. Pat. Nos. 3,140,249; 3,140,251, 3,140,253 and 3,702,886.

Following contact with a solution of the desired replacing cation, the zeolite is then preferably washed with water and dried at a temperature ranging from 150° to about 600° F. and thereafter calcined in air or other inert gas at temperatures ranging from about 500° to 1500° F. for periods of time ranging from 1 to 48 hours or more.

It is also possible to treat the zeolite with steam at elevated temperatures ranging from 800° F. to 1600° F. and preferably 1000° F. to 1500° F., if such is desired. The treatment may be accomplished in atmospheres consisting partially or entirely of steam.

A similar treatment can be accomplished at lower temperatures and elevated pressures, e.g., 350°–700° F. at 2 to about 200 atmospheres.

As previously stated, the alkylation catalysts described herein comprise a zeolite of the aforedescribed type in combination with a Lewis acid. A Lewis acid is generally considered to be a molecule which is capable of combining with another molecule or ion by forming a covalent chemical bond with two electrons from the second molecule or ion, that is to say, the Lewis acid is an electron acceptor. Examples of Lewis acids include boron trifluoride ($BF_3$) antimony pentafluoride ($SbF_5$) and aluminum chloride ($AlCl_3$). The present invention contemplates the use of all Lewis Acids such as those set forth in "Friedel-Crafts and Related Reactions", Interscience Publishers, Chapters III and IV (1963), which is incorporated by reference. Boron trifluoride is preferred for use in the alkylation process of this invention. In general, the aforementioned Lewis acid will be present in the alkylation zone in an amount which exceeds that required to saturate said zeolite catalyst composition considered not only as the zeolite per se but as any other material, e.g., binder or matrix material, which might be associated with the zeolite. Thus, the reaction environment will contain $BF_3$ over and above the amount sorbed or taken up by the zeolite and any binder with which the zeolite might be composited.

The operating temperature of the alkylation process herein can extend over a fairly broad range, e.g., from about −40° to about 500° C. and is preferably within the range of from about −40° C. to about 250° C. The practical upper operating temperature will often be dictated by the need to avoid an undue occurrence of undesirable side reactions.

The pressures employed in the present process can extend over a considerably wide range, e.g., from subatmospheric to about 5000 psig, preferably to about 500 psig.

The amount of catalyst used in the present process can be varied over relatively wide limits. In general, the amount of catalyst as measured by the weight hourly space velocity of the olefin can range from about 0.01 to about 100. It will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethylene, propylene, butene-1, butene-2, isobutylene, pentenes, hexenes, heptenes and octenes. Particularly preferred are $C_3$ and $C_4$ olefins and mixtures thereof.

In general, the relative molar ratio between the isoparaffin reactant and the olefin alkylating agent in the combined hydrocarbon feed can be from about 1:1 to about 50:1 and is preferably in the range of from about 5:1 to about 25:1.

A critical requirement of the improved alkylation process herein is that water be added to the alkylation reactor, e.g., at a rate of from about 0.1 ppmw to about 1 wt %, based upon total hydrocarbon feed rate preferably at a rate of from about 0.1 ppmw to about 500 ppmw. The water can be supplied as such or by a feed material which provides water under the alkylation conditions selected. Suitable water-forming materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms as, for example, methanol, ethanol, isopropanol, t-butyl alcohol and isopentyl alcohol. The water and/or water-producing material can be added directly to the reactor, e.g., as part of the feed and/or it can be incorporated in the zeolite, either by direct contact therewith or by exposing the zeolite to an atmosphere of water and/or water-forming material. For example, when the added water and/or water-forming material is preintroduced into the zeolite catalyst, the amount of water and/or water-forming material taken up by the catalyst can be made to vary from about 0.5 to about 25, and preferably from about 1 to about 10, weight percent of the catalyst.

It will be appreciated by those skilled in the art that the particular operating conditions employed in the present process will depend on the specific alkylation reaction being effected. Such conditions as temperature, pressure, space velocity and molar ratio of the reactants will have important effects on the overall process. The operating conditions of the alkylation process can be varied as to provide for operation in the gaseous phase, liquid phase, or mixed liquid-vapor phase depending upon the desired product distribution, degree of alkylation, and so forth.

A suitable system for carrying out the improved alkylation process of this invention on a continuous basis is shown in the annexed figure of drawing. As shown in the drawing, water and/or a water-producing material such as methanol is introduced through line 1 to a stream containing isobutane and propylene and/or butenes along with some normal butane introduced through line 2 to stirred reactor 3 containing a zeolite catalyst. $BF_3$ is introduced as needed from holding tank 5 through line 6 into the reactor. The amount of $BF_3$ introduced is such as to exceed that which is required to saturate the zeolite catalyst (as well as any binder or matrix material with which the zeolite might be composited). Catalyst slurry is removed from the reactor and is introduced to settling vessel 4, the recovered zeolite catalyst thereafter being recycled to the alkylation reactor via line 9. The hydrocarbon product mixture is removed from the settling vessel through line 10 and introduced into $BF_3$ stripper 11 from which $BF_3$ is removed as overhead through line 12 and recycled through line 13 to $BF_3$ holding tank 5. The remaining hydrocarbon product mixture is withdrawn from the $BF_3$ stripper through line 14. A portion of such hydrocarbon product mixture is introduced via lines 15 and 16 to fractionator 17. Unreacted isobutane is removed as overhead through line 18 and recycled through line 19 to the reactant feed stream line 2. Desired $C_{5+}$ alkylate product is withdrawn from the bottom of fractionator 17 through line 20. Any normal butane may be withdrawn from the fractionator through line 21. The remaining portion of the hydrocarbon product mixture passing through line 14 from BF$_3$ stripper 11 is conducted through line 22 to depropanizer 23 from which propane and lighter products are removed as overhead through line 24. Heavier components are removed as bottoms through line 25 and recycled via lines 26 and 16 to fractionator 17. Isobutane is removed from depropanizer 23 through line 27 and recycled through lines 28 and 19 to the initial reactant feed line 2.

The following examples will serve to illustrate the process of the invention without limiting it.

EXAMPLE

Two unbound zeolite Beta catalysts containing 6 and 16 weight percent water, respectively, were employed in the alkylation of isobutane with butene-1. The varying water contents were obtained by exposing separate portions of the zeolite catalyst to low and high moisture content atmospheres.

In each case, 10 grams of zeolite Beta (100% solids basis) is placed in the 300 ml autoclave reactor, and about 300 ml of isobutane is charged to fill the reactor. The resulting mixture is cooled to 0° C. with constant stirring at 1900 rpm and BF$_3$ gas is introduced into the reactor. After BF$_3$ breakthrough is observed, the BF$_3$ flow rate is then reduced to a level equivalent to 3 wt % of total hydrocarbon feed rate. At this point, a 10/1 isobutane/butene-1 mixture is continuously fed into the reactor to initiate the catalytic alkylation. The operating conditions are 150 psig, 0° C., 1900 RPM, 1.2 WHSV based on olefin and 3.0 wt % BF$_3$ based on total hydrocarbon feed. The product is continuously withdrawn from the reactor and is weathered to atmospheric pressure via a back pressure regulator and then sent to a receiver which is kept at 0° C. Periodically, the product is drained from the receiver and weathered at room temperature prior to analysis.

An on-line gas chromatograph coupled with an automatic sampling device is used to monitor the course of the alkylation reaction. All reported clear octane numbers are measured. The isobutane (C.P. grade), isobutane/olefin mixture and BF$_3$ (C.P. grade) are all used without further purification.

Tables 1 and 2 show the yield/octane results for the low and high water-containing zeolite Beta catalysts, respectively. In both cases the $C_{5+}$ yield data indicate that alkylation is essentially complete. As the data show, a significant improvement in the alkylate quality was observed for the 16 weight percent water-content zeolite Beta catalyst. Specifically, the octane numbers from the high water-content catalyst are substantially higher over the course of the experiment. In addition, the $C_{9+}$ content of the alkylate product is reduced with the higher moisture content catalyst.

TABLE 1

Performance of "Low Water Content" Zeolite-Beta (6 Wt. % H$_2$O) For Isobutane/Butene-1 Alkylation

| Time on Stream, hr. | 4 | 10 | 20 |
|---|---|---|---|
| Yield, g $C_{5+}$/g Olefin Converted | 2.1 | 2.3 | 2.2 |
| Yields in $C_{5+}$, wt % | | | |
| $C_5$–$C_7$ | 0.6 | 1.0 | 1.7 |
| $C_8$ | 88.2 | 89.9 | 86.4 |
| $C_{9+}$ | 11.2 | 9.1 | 11.9 |
| Octane | | | |
| RON + O | 71.0 | 71.8 | 67.3 |
| MON + O | 76.1 | 77.6 | 70.3 |

TABLE 2

Performance of "High Water Content" Zeolite-Beta (16 wt. % H$_2$O) For Isobutane/Butene-1 Alkylation

| Time on Stream, hr. | 4 | 8 | 18 |
|---|---|---|---|
| Yield, g $C_{5+}$/g Olefin Converted | 2.2 | 2.3 | 1.9 |
| Yields in $C_{5+}$, wt % | | | |
| $C_5$–$C_7$ | 1.8 | 0.7 | 1.5 |
| $C_8$ | 90.3 | 95.9 | 94.4 |
| $C_{9+}$ | 7.9 | 3.4 | 4.1 |
| Octane | | | |
| RON + O | 77.1 | 79.3 | 86.0 |
| MON + O | 80.1 | 80.9 | 81.4 |

What is claimed is:

1. An alkylation process for producing high octane gasoline comprising reacting a stream of an isoparaffin containing from 4 to 20 carbon atoms with a stream of an olefin containing from 2 to 12 carbon atoms at a temperature from about −40° C. to about 500° C. and at a pressure in the range of subatmospheric to about 5000 psig in an alkylation zone using a reaction mixture wherein a molar ratio of the isoparaffin to the olefin in the combined hydrocarbon feed is from about 1:1 to about 50:1 in the presence of added water and in contact with an alkylation catalyst comprising a Lewis acid and a bound and/or unbound large pore zeolite.

2. The process of claim 1, wherein the isoparaffin contains from 4 to 6 carbon atoms and the olefin contains from 2 to 6 carbon atoms.

3. The process of claim 1, wherein the Lewis acid is BF$_3$, BCl$_3$, SbF$_5$ and/or AlCl$_3$.

4. The process of claim 1, wherein the Lewis acid is BF$_3$.

5. The process of claim 1 wherein the zeolite is selected from the group consisting of ZSM-3, ZSM-4, ZSM-12, ZSM-18, ZSM-20, zeolite Beta, zeolite L, mordenite, faujasite and zeolite Y.

6. The process of claim 1, wherein the catalyst is BF$_3$/zeolite Beta.

7. The process of claim 1, wherein the reaction is conducted under sufficient pressure to maintain at least one of the reactants in the liquid phase.

8. The process of claim 1, wherein the molar ratio of the isoparaffin to the olefin is from about 5:1 to about 25:1.

9. The process of claim 1, wherein the isoparaffin is isobutane and the olefin is propylene and/or butene.

10. The process of claim 1, wherein the water and/or water-producing material is preintroduced into the catalyst.

11. The process of claim 1, wherein the water and/or water-producing material is cofed with the reactants.

12. The process of claim 10, wherein the amount of water preintroduced into the catalyst ranges from about 0.5 to about 25 percent by weight of the catalyst.

13. The process of claim 10, wherein the amount of water preintroduced into the catalyst ranges from about 1.0 to about 10 percent by weight of the catalyst.

14. The process of claim 11, wherein the amount of water ranges from about 0.1 ppmw to about 1 weight percent based upon the total hydrocarbon feed rate.

15. The process of claim 11, wherein the amount of water ranges from about 0.1 ppmw to about 500 ppmw based upon the total hydrocarbon feed rate.

16. The process of claim 1, wherein water is added intermittently to the reaction.

17. The process of claim 1, wherein reaction temperature is from about −40° C. to about 250° C.

18. The process of claim 1, wherein the weight hourly space velocity of that olefin is from about 0.01 to about 100.

19. The process of claim 1 where the zeolite is contained in a matrix.

20. The process of claim 1 wherein the Lewis acid is present in an amount in excess of that required to substantially saturate the zeolite and any binder or matrix material with which the zeolite may be associated, and in which the excess level of Lewis acid is maintained by continuous or intermittent introduction of fresh and/or recycled Lewis acid in the alkylation zone.

21. An alkylation process for producing high octane gasoline comprising reacting a stream of an isoparaffin containing from 4 to 20 carbon atoms with a stream of an olefin containing from 2 to 12 carbon atoms at a temperature from about −40° C. to about 250° C. and at a pressure from about subatmospheric to about 500 psig in an alkylation zone into which water is introduced in an amount from about 0.1 ppmw to about 500 ppmw water based on total hydrocarbon feed at a molar ratio of the isoparaffin to the olefin from about 5:1 to about 25:1 in contact with an alkylation catalyst comprising a Lewis acid and bound and/or unbound large pore zeolite.

22. A process according to claim 21 in which the weight hourly space velocity of the olefin feed stream is from 0.01 to 100.

23. A process according to claim 22 in which the water is present in the alkylation zone in an amount of from about 0.1 to about 500 ppmw, based on the total hydrocarbon feed to the alkylation zone.

* * * * *